United States Patent [19]

Tanaka

[11] 4,198,243

[45] Apr. 15, 1980

[54] COATING COMPOSITION CONTAINING A LIQUID GLYCOL

[76] Inventor: Asami Tanaka, 4840 Foster St., Skokie, Ill. 60077

[21] Appl. No.: 870,655

[22] Filed: Jan. 19, 1978

[51] Int. Cl.$^2$ ............................................... C09K 3/00
[52] U.S. Cl. ...................................... 106/19; 106/35; 433/24; 433/70
[58] Field of Search .................. 106/20, 22, 23, 31, 106/19, 35; 32/19, 15, 8

[56] References Cited

U.S. PATENT DOCUMENTS

| | | | |
|---|---|---|---|
| 2,112,762 | 3/1938 | Chatfield | 106/19 X |
| 2,171,759 | 9/1939 | Meyer | 32/2 |
| 2,589,306 | 3/1952 | Steiner | 106/22 R |
| 2,623,827 | 12/1952 | Moos | 106/23 |
| 2,633,637 | 4/1953 | Lucia | 32/19 |
| 2,674,797 | 4/1954 | Skinner | 32/19 |
| 2,752,681 | 7/1956 | Jankelson | 32/19 |
| 2,966,417 | 12/1960 | Anderson | 106/22 |
| 3,118,230 | 1/1964 | Trapozzano | 32/19 |
| 3,421,223 | 1/1969 | Stark | 32/19 |
| 3,627,546 | 12/1971 | Coppeta | 106/19 |
| 3,672,842 | 6/1972 | Florin | 106/31 X |
| 3,813,781 | 6/1974 | Forgione | 32/19 |
| 3,873,687 | 3/1975 | Demko | 106/19 X |
| 3,914,131 | 10/1975 | Hutchinson | 106/19 X |
| 3,918,160 | 11/1975 | Friedman | 32/19 |
| 3,959,881 | 6/1976 | Kokal | 32/19 |

FOREIGN PATENT DOCUMENTS

| | | | |
|---|---|---|---|
| 645133 | 7/1962 | Canada | 106/19 |
| 52-865363 | 6/1977 | Japan . | |
| 1343704 | 1/1974 | United Kingdom | 106/19 |

OTHER PUBLICATIONS

Warth, *The Chemistry and Technology of Waxes*, Second Edition, published by Reinhold Publishing Corporation, N.Y., 1956, (pp. 88–93, "Chemical Composition of Bees Wax").

Tanaka, published Japanese application No. 147,196 with translation.

*Primary Examiner*—Howard E. Schain
*Attorney, Agent, or Firm*—Neuman, Williams, Anderson & Olson

[57] ABSTRACT

A composition for marking the contact points on the occlusal surface of a dental restorative or a natural tooth and for use in evaluating the mode of contact between occluding teeth.

35 Claims, No Drawings

COATING COMPOSITION CONTAINING A LIQUID GLYCOL

BACKGROUND OF THE INVENTION

1. Field of the Invention

This application relates generally to means for evaluating the contact between occluding teeth and more particularly concerns a composition for marking the contact points on the occlusal surface of a dental restorative or of one natural tooth of a pair of occluding teeth.

2. Description of the Prior Art

In preparing various types of dental restoratives from mouth impressions and in improving occlusion of certain or all of the natural teeth, difficulty has oftentimes been experienced in accurately contouring the occlusal surface of the dental restorative or of the natural tooth. Improper contouring of such occlusal surfaces can cause paradental diseases, such as phyorrhea alveolaris.

Prior art methods to facilitate such contouring have generally employed bite paper, typewriter ribbon, wax or other similar material which was inserted between the occlusal surfaces in order to determine the contact points or the mode of contact between the upper and lower occlusal surfaces of a pair of occluding teeth. Use of such devices does not permit accurate evaluation of the three-dimensional contact between the occlusal surfaces of such teeth. The relatively large thickness of each of such devices prevents the occlusal surfaces from attaining their natural and properly occluding relationship and results in erroneous marking of points which are not truly the contact points between the occlusal surfaces. Further, such devices prevent visual observance of the biting contact between the occlusal surfaces and thereby hinder evaluation of such contact.

In addition, when used, such devices quickly become dry and brittle and, in such a state, make it extremely difficult to accurately mark the contact points between the occlusal surfaces. Such devices also cause an inordinate amount of strain in certain areas of a restorative occlusal surface whereby subsequent removal of the strain therefrom requires a difficult and awkward manipulation. Moreover, use of such devices is often difficult and time consuming. For example, it is impossible to insert more than one of such devices, such as two different kinds of bite papers, between the occlusal surfaces of a given pair of occluding teeth at the same time. Consequently, simultaneous examination of multiple biting movements is not possible, necessitating prolonged examination time.

Modern dentistry requires improved techniques for accurate evaluation of the contact points between occlusal surfaces. A method which avoids the aforenoted shortcomings of such prior art methods and makes possible the more accurate evaluation of the mode of contact between a pair of occluding teeth has been disclosed in applicant's Japanese Pat. No. 865,363, which issued June 23, 1977. In that method, a thin coating material is applied to the occlusal surface of one tooth of a pair of occluding teeth by means of a small brush. When both members of the pair of occluding teeth are brought into occluding relationship with each other, the coating material transfers at the points of contact from the coated occlusal surface to the uncoated occlusal surface. If the bite surface is too high, a bite plane correction can be made by scraping or filing the marked contact points to the extent necessary to achieve the proper bite contact.

An improved method of utilizing a plurality of transferable coatings of contrasting colors for marking contact points at predetermined areas on the occlusal surface of at least one pair of occluding teeth is the subject of applicant's copending U.S. patent application filed concurrently herewith and entitled Method of Marking Contact Points on the Occluding Surface of a Dental Restorative, Ser. No. 870,654, filed Jan. 19, 1978. In the method of the copending U.S. application, a coating of each color is applied to predetermined areas of the occlusal surface of a tooth or tooth impression molding. The coated occlusal surface is then brought into occluding relationship with a natural tooth or a dental restorative whereupon a portion of the previously applied coating in each predetermined area is transferred to the corresponding predetermined area of the occlusal surface of the natural tooth or restorative, but only at each contact point located within the corresponding predetermined area.

The coating composition of applicant's Japanese patent contains 10–30 percent of weight of a fluid paraffin, 30–40 percent by weight of vaseline, 10–20 percent by weight of glycerin and organic coloring. Such composition has certain properties which prevent the utilization of the methods of the aforesaid Japanese patent and of the aforesaid copending U.S. patent application to their maximum extent. First, although such composition can be applied as a thin coating of less than about half the thickness of the standard bite paper, thereby permitting visual examination of the contact points and a more accurate evaluation thereof than bite paper, this coating still has a finite thickness which prevents an even more accurate evaluation which an even thinner coating would facilitate. In addition, such coating composition is relatively insoluble and/or nondispersible in water, thereby precluding removal from the coated areas and contact points by a water rinse. It is extremely desirable to be able to remove the coating material by a water rinse, particularly when the coating is on a tooth in the mouth. In addition, the components of such composition are not readily compatible, and vigorous mixing conditions are required to fabricate the composition. The composition of the present invention is an improvement over, and otherwise has all of the advantageous properties of, the coating composition of the aforesaid Japanese patent.

OBJECTS OF THE INVENTION

It is a general object of this invention to provide an improved coating composition which overcomes the aforenoted shortcomings.

It is therefore an object of the present invention to provide a coating composition which facilitates the ready location and accurate correction of contour imperfections which exist on the occlusal surface of a natural tooth or dental restorative.

It is also an object of the present invention to provide a coating composition which is capable of being smeared on an occlusal surface of a natural tooth or dental restorative as a coating having a nominal thickness so as not to impair an accurate occluding relationship.

Another object of this invention is to provide a coating composition which is sufficiently water soluble or dispersible to permit its removal from the occlusal surface by a water rinse.

It is a further object of the invention to provide a coating composition which is capable of application to one occlusal surface as a transferable coating which remains in operative state regardless of the number of times the coated surface is brought into contact with a second occlusal surface.

Other objects and advantages of the invention will become apparent upon reading the following detailed description and appended claims.

SUMMARY OF THE INVENTION

These objects are achieved by an improved coating composition which comprises a liquid glycol as its base, a coloring agent, and a thickening agent.

In use, the coating composition is applied as a thin coating to the occlusal surface of one tooth of a pair of occluding teeth and then the coated tooth and the uncoated tooth of said pair are brought into occluding relationship so that a portion of the coating is transferred to the occlusal surface of the uncoated tooth as a thin marking at each contact point between the teeth. The coloring agent is employed so that such marking has sufficient color intensity to permit visual location of the contact points on the occlusal surface of the uncoated tooth.

The thickening agent facilitates the fabrication of the coating composition in the form of a readily deformable paste which is capable of being smeared as a thin, immobile transferable coating on the occlusal surface of the coated tooth so that, when the pair of occluding teeth is brought into occluding relationship, a portion of the coating in turn is capable of being transferred to the occlusal surface of the uncoated tooth as a thin, immobile marking at each contact point between the teeth. The coating is sufficiently thin to permit the occluding teeth to enter into a substantially unimparied occluding relation. The mixture of the liquid glycol and the thickening agent also serves as a carrier for the coloring agent.

The improved composition in the form of the coating and marking is removable from the teeth by a water rinse.

DETAILED DESCRIPTION OF THE PREFERRED EMBODIMENTS

The coating composition of this invention possesses numerous properties which are advantageous in locating contour imperfections which exist on the occlusal surface of a natural tooth or dental restorative. It will of course be appreciated that the coating composition of this invention can be used to locate contour imperfections in any dental operation, for example, fabrication of a dental restorative, precision attachment of a bridge or adjustment of the seating of a crown or of the fitting of pontics to the tissue surface. For the sake of simplicity, the word "tooth" is used to indicate a natural tooth, a dental restorative or an impression molding of a natural tooth, and the phrase "pair of occluding teeth" indicates either a pair of occluding natural teeth or a natural tooth and an occluding dental restorative or a dental restorative and an impression molding of an occluding natural tooth.

This invention is a readily deformable, colored paste which is capable of being picked or scooped up, for example, by a small brush and thereby smeared as a thin, colored, immobile and transferable coating on the occlusal surface of one tooth of a pair of occluding teeth. The brush is generally dipped into the coating composition and then is rubbed against a palette in order to obtain a uniform distribution of the composition on the tip of the brush. Then a thin coate of the coating composition is smeared by the brush onto the occlusal surface of the tooth.

This coating is immobile in that it does not flow from the point of its application on the occlusal surface. Nevertheless, the coating composition is such that, when the coated tooth and the uncoated tooth of the pair of occluding teeth are brought into occluding relationship, a portion of the coating on the coated tooth is transferred to the occlusal surface of the uncoated tooth as a thin, colored and similarly immobile marking at each point of contact between such teeth. The color intensity of such marking is sufficient to permit visual location of each such contact point.

The pasty consistency of this coating composition permits it to be smeared as a coating of only nominal thickness on the occlusal surface of a tooth. The coating is typically approximately 5 microns thick. Such coating is sufficiently thin as not to impair a proper occluding relationship between the pair of occluding teeth. Generally, in addition, this coating composition is sufficiently water soluble or water dispersible to permit the coating and marking to be removed from the teeth by a water rinse. The coating composition can also be substantially completely burned off or removed by heating at temperatures between 1200° and 1300° F., leaving amounts of residue so small as not to interfere with the fabrication of a ceramic dental restorative.

The coating composition of this invention contains as the base a liquid glycol selected from the group consisting of a glycol containing n hydroxyl groups and from n to n+2 carbon atoms where n is 2 to 10, a glycol having the formula HO—$(C_2H_4O)_a$—H where a is 3 to 20 and a glycol having the formula HO—$(C_3H_6O)_b$—H where b is 2 to 15. Examples of suitable glycols are ethylene glycol, propylene glycol, glycerin, sorbitol, diethylene glycol, dipropylene glycol, diglycerin, polyethylene glycol and polypropylene glycol. Preferably glycerin or a mixture of glycerin and propylene glycol is employed. This component is employed at a concentration of at least about 50 percent, perferably at least about 65 percent, and less than or equal to about 90 percent, preferably less than or equal to about 85 percent, by weight of the composition.

In addition, a coloring agent is required. Any suitable conventional coloring agent which can be dissolved and/or suspended in the coating composition can be employed. Suitable examples of the coloring agent include food coloring, water soluble dyes, oil soluble dyes, fluorescent dyes (in which case an ultra-violet light is used for inspection) and organic and inorganic pigments. If an inorganic coloring agent is employed in an application wherein the coating composition is to be removed by heating, the quantity of ash remaining must be sufficiently small as not to interfere in such application. Preferably, food coloring ("F D and C colors") is employed. Red, green and yellow colors have been found to be particularly suitable. The concentration of the coloring agent to be used in the coating composition is that which is effective in producing sufficient color intensity in the coating and markings to permit ready visual location of the contact points. It has been found that concentrations of the coloring agent of from about 0.05 percent to about 3.0 percent by weight and preferably from about 0.1 percent to about 2.0 percent by weight of the composition are sufficient to achieve the desired color intensity.

A thickening agent is required so that the mixture of the glycol base, the coloring agent and the thickening agent is in the form of a readily deformable paste which is capable of being smeared as a thin, immobile coating on the occlusal surface of one tooth of a pair of occluding teeth. A portion of this coating must in turn be capable of being transferred to the occlusal surface of the uncoated tooth when the pair of occluding teeth is brought into occluding relationship, as a thin marking at only the contact points between the occluding teeth. The coating and marking must be sufficiently thin as not to impair a proper occluding relationship between the pair of occluding teeth. The thickening agent also serves, in combination with the glycol base, as a carrier for the coloring agent.

The suitability of a particular material for use as the thickening agent is determined by the acceptability of the properties of the coating composition made from such material. Since mainly the physical properties of a material are of importance in determining its suitability as the thickening agent, great latitude is permitted in the choice of the thickening agent and concentration thereof. Generally, the coating composition of this invention contains thickening agent at a concentration of at least about 10 percent, preferably at least about 15 percent, less than or equal to about 50 percent, preferably less than or equal to about 35 percent, by weight.

The thickening agent can be a solid glycol ester of a fatty acid containing from 12 to 22 carbon atoms and of a glycol selected from the group consisting of a glycol containing n hydroxyl groups and from n to n+2 carbon atoms where n is 2 to 10, a glycol having the formula $HO-(C_2H_4O)_d-H$ where d is 3 to 27 and a glycol having the formula $HO-(C_3H_6O)_g-H$ where g is 2 to 20. The ester must have at least one free hydroxyl group. Also useful is a solid ethoxylated ester formed by the reaction of 2 to 30 moles of ethylene oxide and one mole of such solid glycol ester. Examples of suitable such esters are the monostearate, monopalmitate and monolaurate of ethylene glycol, propylene glycol, glycerin, sorbitol, sucrose, diethylene glycol, dipropylene glycol, diglycerin, sorbitan, polyethylene glycol and polypropylene glycol, and the ethoxylated derivatives of such esters. Preferably glyceryl monostearate is employed. The ester is employed at a concentration of at least about 10 percent, preferably at least about 15 percent, and less than or equal to about 50 percent, preferably less than or equal to about 35 percent, by weight of the coating composition.

Alternatively, the thickening agent can be a mixture of a glycol ester or ethoxylated glycol ester and at least one material selected from the group consisting of a fatty acid, a fatty acid ester, a fatty alcohol, an ethoxylated fatty alcohol, an aliphatic hydrocarbon oil or wax, and an alkanolamine.

Each such glycol ester in such mixture has at least one free hydroxyl group and is an ester of a fatty acid containing 12 to 22 carbon atoms and of a glycol selected from the group consisting of a glycol containing n hydroxyl groups and from n to n+2 carbon atoms, where n is 2 to 10, glycol having the formula $HO-(C_2H_4O)_x-H$ where x is 3 to 27 and a glycol having the formula $HO-(C_3H_6O)_y-H$ where y is 2 to 20. The ethoxylated ester in such mixture is a reaction product of 2 to 30 moles of ethylene oxide and one mole of such glycol ester. Examples of suitable such esters include the monooleate, monostearate, monopalmitate and monolaurate of ethylene glycol, propylene glycol, glycerin, sorbitol, sucrose, diethylene glycol, dipropylene glycol, diglycerin, sorbitan, polyethylene glycol and polypropylene glycol, and the ethoxylated derivatives of such esters. Preferably glyceryl monostearate is employed. Such ester or ethoxylated ester is employed at a concentration of at least about 3 percent, preferably at least about 5 percent, and less than about 50 percent, preferably less than or equal to about 35 percent, by weight of the coating composition.

The fatty acid component contains from 12 to 22 carbon atoms and, if employed in this mixture, is at a concentration of at least about 1 percent, preferably at least about 2 percent, and less than or equal to about 30 percent, preferably less than or equal to about 15 percent, by weight of the coating composition. Suitable acids include stearic, palmitic, lauric, myristic, oleic and linoleic acids. Preferably stearic acid is employed.

The fatty acid ester is an ester of a fatty acid containing 10 to 22 carbon atoms and of an aliphatic monohydroxy alcohol containing from 1 to 4 carbon atoms. Examples of suitable such fatty acid esters are methyl laurate, isopropyl myristate, isopropyl palmitate, n-butyl stearate, isopropyl isostearate and n-butyl oleate. Preferably, isopropyl palmitate is employed. The ester, if present in this mixture, is employed at a concentration of at least about 1 percent and less than or equal to about 5 percent, preferably less than or equal to about 3 percent, by weight of the coating composition.

The fatty alcohol contains from 10 to 30 carbon atoms and is one which is theoretically obtainable by the substitution of —OH for —OOH in the corresponding fatty acid. The alcohol, if employed in this mixture, is at a concentration of at least about 0.1 percent, preferably at least about 2 percent, and less than or equal to about 5 percent, by weight of the coating composition. Suitable fatty alcohols include palmityl, stearyl, myristyl, oleyl, cetyl and lauryl alcohols. Preferably, cetyl alcohol is employed.

The ethoxylated fatty alcohol is a product formed by the reaction of 2 to 30 moles of ethylene oxide and one mole of such fatty alcohol containing from 10 to 30 carbon atoms. Suitable examples include laureth-4, laureth-20, laureth-23, steareth-20, ceteth-10, ceteth-20, ceteth-28, polyoxyethylene (10) oleyl ether and polyoxyethylene (20) oleyl ether. Preferably laureth-23 is employed. If present in the mixture, the ethoxylated fatty alcohol is at a concentration of at least about 0.3 percent, preferably at least about 0.5 percent, and less than or equal to about 2 percent, preferably less than or equal to about 1 percent, by weight of the coating composition.

The aliphatic hydrocarbon oil or wax, if employed in this mixture, is at a concentration of at least about 1 percent, preferably at least about 4 percent, and less than or equal to about 10 percent, preferably less than or equal to about 7 percent, by weight of the coating composition. Preferably, the oil or wax is a highly refined aliphatic mineral oil of U.S.P. grade or a low melting, refined aliphatic microcrystalline or paraffin wax.

The alkanolamine is a secondary or tertiary amine containing from 4 to 9 carbon atoms, with each alkanol moiety containing 2 to 3 carbon atoms. Suitable alkanolamines include diethanolamine, diisopropanolamine, triethanolamine, triisopropanolamine and N-methyldiethanolamine. Preferably triisopropanolamine is employed. In addition, certain primary amines including the ethoxylated derivatives of isopropanolamine, namely $HO(C_2H_4O)_2C_3H_6NH_2$ (polyglycolamine) and $H_2NC_3H_6(C_2H_4O)_2-C_3H_6NH_2$ (polyglycoldiamine) are also suitable. The amine, if present in the mixture, is employed at a concentration of at least about 1 percent, and less than or equal to about 10 percent, preferably less than or equal to about 3 percent, by weight of the coating composition.

Alternatively, the thickening agent can be a mixture of a solid fatty acid and an alkanolamine. The fatty acid in this mixture contains from 12 to 22 carbon atoms and is at a concentration of at least about 7 percent, preferably at least about 12 percent, and less than or equal to about 40 percent, preferably less than or equal to about 30 percent, by weight of the coating composition. Suitable acids include stearic, palmitic, lauric and myristic acids. Preferably stearic acid is employed.

The alkanolamine in this mixture is a secondary or tertiary amine containing from 4 to 9 carbon atoms, with each alkanol moiety containing 2 to 3 carbon atoms. Suitable alkanolamines are diethanolamine, diisopropanolamine, triethanolamine, triisopropanolamine and N-methyldiethanolamine. Preferably triisopropanolamine is employed. In addition, certain primary amines including the ethoxylated derivatives of isopropanolamine, namely $HO(C_2H_4O)_2C_3H_6NH_2$ (polyglycolamine) and $H_2NC_3H_6(C_2H_4O)_2C_3H_6NH_2$ (polyglycoldiamine) are also suitable. The amine is present at a concentration which is about 0.1 to 1.0 of that needed to exactly neutralize the solid fatty acid in the mixture.

EXAMPLE 1-33

Compositions which are suitable for use in marking the contact points on the occlusal surfaces of a pair of occluding teeth are prepared by mixing various combinations of the components shown in Tables 1 and 2. In each example, the components listed in the tables make up 100 percent of the coating composition. The components in each example are added to a mixing vessel in any sequence and mixed manually. Compositions having the desired properties noted above are obtained after a short period of mixing. Generally, low heating at a temperature in the range of 30°-70° C. is used to facilitate the mixing process.

EXAMPLE 34

Three hundred milliliters of Vaseline ® Brand Intensive Care ® Lotion For Overdry Skin (manufactured by Chesebrough Ponds, Inc.), weighing about 294 grams was heated at about 100° C. to drive off at least the majority of the water therein. Vaseline ® Brand Intensive Care ® Lotion For Overdry Skin is made up of water, glycerin, glyceryl stearate, stearic acid, mineral oil, cetyl alcohol, laureth-23, triisopropanolamine, lanolin, isopropyl palmitate, fragrance, methylparaben, propylene glycol, carbomer-934, propylparaben, simethicone, trisodium ethylene diamine tetraacetate, D and C red No. 19, and D and C yellow No. 10. The remaining material was a thick paste which weighed about 43 grams. To 43 grams of the paste, 130 milliliters of glycerin, weighing about 170 grams, and 3-4 grams of red food color were added, and the mixture was stirred manually until a product of uniform consistency was obtained. The additions and stirring were performed at a temperature of about 40°-50° C. which facilitated the stirring operation.

TABLE 1

| Component | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| glycerin | 75 | 75 | 75 | 75 | 75 | 60 | 85 | 40 | 50 | 80 | 75 | 75 | 75 | 75 | 75 | 75 | 75 | 75 | 89 |
| glyceryl monostearate | 25 | | 12 | 12 | 11 | 30 | 15 | 25 | 10 | 12 | 18 | 20 | 10 | 10 | | | | | 10 |
| stearic acid | | 21 | 10 | 10 | 11 | | | | 10 | 4 | | | | 11 | 10 | 10 | 10 | 11 | 10 |
| mineral oil | | | | | | 5 | | | 2 | 1.5 | 4 | | | | | | | | |
| cetyl alcohol | | | | | | | | | 1 | | 2 | 1 | | | | | | | |
| laureth −23 | | | | | | | | | | | 1 | 1 | 1 | 1 | | | | 1 | |
| triisopropylamine | | | | 3 | 3 | | | | 3 | 1.5 | | | 3 | 1.5 | | | | 1.5 | |
| isopropyl palmitate | | | | | 5 | | | | 5 | 1 | | 3 | 1 | | | | | 1 | |
| propylene glycol | | | | | | | 35 | 20 | | | | | | | | | | | |
| triethanolamine | | 4 | 3 | | | | | | | | | | | 3 | 3 | | | 3 | |
| glyceryl monoleate | | | | | | | | | | | | | | | 12 | 12 | 11 | 10 | |
| FD&C red No. 1[1] | | | | | | | | | | | 0.8 | | | | | | | | |
| FD&C blue No. 1[2] | | 0.07 | | | | | | | | | | | | | | | | | |
| FD&C violet No. 1[3] | | | | | | | | | 1 | | | | | | | | | | |
| oil black No. 3[4] | | | | | | | | | | | | | | | 0.1 | | | | |
| FD&C yellow No. 5[5] | | | | | | | 0.2 | | | | | | | | | | | | |
| D&C blue No. 4[6] | | | | | | | | | | | | | | | | | | | 1 |
| rhodamine 6GND[7] | | | | | | | | | | | | | | | | | | 2 | |
| D&C green No. 5[8] | | | 3 | | | | | | | | | | | | | | | | |
| phthalocyanine blue[9] | | | | | | | | | | | | | | 2.5 | | | | | |
| D&C red No. 6[10] | 0.07 | | | | | | | | | | | | | | | | | | |
| D&C blue No. 6[11] | | | | | | | | | 1.5 | | | | | | | | | | |
| victoria blue BO[12] | | | | | | | | | | | | 1.5 | | | | | | | |
| D&C yellow No. 7[13] | | | | | | | | | | | | | | | | 2.8 | | | |
| oil black[14] | | | | | 0.1 | | | | | | | | | | | | | | |
| oil green[15] | | | | | | | | | | | | | | | | 2 | | | |
| oil orange No. 31[2] | | | | | | 5 | | | | | | | | | | | | | |
| oil scarlet[17] | | | | | | | | | | | | | | | | | | 0.1 | |
| oil scarlet No. 389[18] | | | | | | | | | | 0.2 | | | | | | | | | |

TABLE 1-continued

| Component | \n Parts by Weight in Example | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| oil violet[19] | | | | | | 0.1 | | | | | | | | | | | | | |

Footnotes
[1] ponceau 3R, index no. 16155
[2] brilliant blue FC2
[3] wool violet 5BN index No. 42640
[4] solvent black 3, index No. 26150
[5] tartrazine, index No. 19140
[6] alphazurine FG, index 63010
[7] index No. 45160
[8] alizurin cyanine green F, index No. 65170
[9] index No. 74160
[10] litholrubin B, index No. 15630
[11] indigo, index No. 73000
[12] index No. 42595
[13] fluorescein
[14] solvent black 7, index No. 50515B
[15] oil green 4B, index No. 61565
[16] solvent yellow 14, index No. 12055
[17] solvent orange 7, index No. 12140
[18] solvent red 1, index No. 12150
[19] solvent violet 13, index No. 60725

TABLE 2

| Component | Parts by Weight in Example | | | | | | | | | | | | | |
|---|---|---|---|---|---|---|---|---|---|---|---|---|---|---|
| | 20 | 21 | 22 | 23 | 24 | 25 | 26 | 27 | 28 | 29 | 30 | 31 | 32 | 33 |
| glycerin | | | | | 20 | | | | 75 | | 25 | | | |
| ethylene glycol | 75 | | | | | 60 | | | | | 34 | | | |
| diethylene glycol | | 75 | | | | | | 20 | | 40 | | 50 | | 40 |
| propylene glycol | | | 80 | | | | | | | | | 15 | | |
| dipropylene glycol | | | | 70 | | | | | | | | | | |
| polyethylene glycol 600[1] | | | | | | 50 | | | | 40 | | | | 40 |
| polyethylene glycol 4000[1] | | | | | | | 20 | | | | | | | |
| polypropylene glycol 600[1] | | | | | | | | 75 | | | | | | |
| sorbitol | | | | | | | | | 40 | | | | 50 | |
| glyceryl monostearate | | | 10 | 15 | | 5 | 10 | 20 | 10 | | | | 10 | |
| glyceryl monooleate | | | | | | | | | | | | 5 | 15 | |
| polyethylene glycol 400[1] monostearate | 20 | | | | | | | | | | | | | |
| ethylene glycol monostearate | | 15 | | 5 | 5 | | | | | | | | | |
| polyethylene glycol 600[1] monolaurate | | | | | 15 | | | | | | | 5 | | |
| polyethylene glycol 1000[1] monooleate | | | | | | | | | | 10 | | | | |
| sorbitan monostearate | | | | | | | | | | | | | | |
| polyoxyethylene (20)[2] sorbitan sesquioleate[3] | | 5 | 5 | 1 | | 2 | 1 | 15 | | | 5 | | | |
| palmitic acid | | | | 5 | | | | | 10 | | 20 | | 15 | 10 |
| lauric acid | | | | | 5 | 10 | | | | 7 | | 15 | | 5 |
| stearic acid | | | | | | | 10 | | | | | | | |
| petrolatum | 1 | | | | | | 1 | | | | 2 | | 2 | |
| simethicone[4] | | 0.2 | | | | | | | | | | | | |
| lauryl alcohol | 1 | | | 1 | 1 | 1 | | 1 | | | 5 | | 1 | |
| stearyl alcohol | | 2 | 2 | | 2 | | 1 | | | | | 3 | | |
| oleyl alcohol | | | | | | | | | | 2 | | | | |
| diethanolamine | | | | | 1 | 2 | 2 | | 3 | 1 | | | | |
| diisopropanolamine | | | | | | | | | | | | 4 | | |
| triethanolamine | | | | | | | | | | 2 | | | | 5 |
| triisopropanolamine | | | | | | | | | | | | | 3 | |
| polyglycoldiamine[5] | | | | | | | | | | | | | | |
| polyglycolamine[6] | | | 1 | 1 | | | | | | | | | | |
| steareth -20 | 1 | | | | | | | 2 | | 2 | | | | |
| ceteth -20 | | 1 | | | 1 | | | | | | 1 | 2 | | |
| laureth -4 | | | 0.5 | 2 | | | | | | | 1 | | 2 | |
| isopropyl myristate | | 1.8 | 1.5 | | 1 | | | | | | 5 | 1 | 2 | |
| n-butyl stearate | | | | 1 | | | | | | | | | | |
| isopropyl isostearate | 2 | | | | | | | 2 | | | | | | |
| FD&C green No. 1[7] | | | | | | | 0.8 | | | | | | | |
| FD&C blue No. 2[8] | | 0.07 | | | | | | | | | | | | |
| D&C brown No. 1[9] | | | | | | | | | | | 0.1 | | | |
| D&C orange No. 4[10] | | | | | 0.2 | | | | | | | | | |
| phthalocyanine green[11] | | | | | | | | | | | | | | 1 |
| D&C yellow No. 11[12] | | | | | | | | | | | | | 2 | |
| carbon black | | | | | 3 | | | | | | | | | |
| oil yellow[13] | | | | | | | | | | 2.5 | | | | |
| oil red[14] | | 0.07 | | | | | | | | | | | | |
| oil black No. 3[15] | | | | | | 1.5 | | | | | | | | |
| D&C red No. 8[16] | | | | | | | | | 1.5 | | | | | |
| D&C orange No. 5[17] | | | | | | | | | | | | | 2.8 | |
| D&C green No. 6[18] | | | 0.1 | | | | | | | | | | | |

TABLE 2-continued

| Component | Parts by Weight in Example | | | | | | | | | | | | | |
|---|---|---|---|---|---|---|---|---|---|---|---|---|---|---|
| | 20 | 21 | 22 | 23 | 24 | 25 | 26 | 27 | 28 | 29 | 30 | 31 | 32 | 33 |
| FD&C green No. 2[19] | | | | | | | 2 | | | | | | | |

Footnotes
[1] approximate average molecular weight
[2] Tween 60 from Imperial Chemical Industries
[3] Arlacel 83 from Imperial Chemical Industries
[4] viscosity of 200 centistokes at 25° C.
[5] Polyglycoldiamine H221 from Union Carbide
[6] Polyglycolamine H161 from Union Carbide
[7] guinea green B, index No. 42085
[8] indigotene, index No. 73015
[9] resorcin
[10] orange II, index No. 12100
[11] index No. 74265
[12] quinoline yellow WS
[13] solvent yellow 3, index No. 1160
[14] solvent red 26, index No. 26120
[15] solvent black 3, index No. 26150
[16] lake red sea, index No. 15585
[17] dibromofluorescein
[18] quinazurin green SS, index No. 61565
[19] light green SF yellowish, index No. 42095

Alternatively, the thickening agent, or at least a component thereof, can be tragacanth gum, ammonium algenate, methyl cellulose, carbomer 934 or hydroxypropyl cellulose. Such materials are particularly desirable if water is present.

Of course suitable preservatives and anti-oxidants may also be present in the coating composition of this invention. Substances suitable for these purposes are well known and include, for example, methylparaben, propylparaben, formaldehyde, p-chloro-m-xylenol, o-phenylphenol, ethylene-diamine-tetraacetic acid or its salts, butylated hydroxyanisole, butylated hydroxytoluene and propylgallate. Such materials can be present at concentrations which are effective to achieve the intended preserving or anti-oxidizing effect, that is, generally from about 0.01 percent to about 0.5 percent, by weight of the coating composition.

Additional materials, such as lanolin or simethicone, which do not interfere in the intended use of the coating composition can also be present.

From the above description it is apparent that the objects of the present invention have been achieved. While only certain embodiments have been set forth, alternative embodiments and various modifications thereof will be apparent from the above description to those skilled in the art and are considered equivalents and within the spirit and scope of the present invention.

Having described the invention, what is claimed is:

1. A coating composition, comprising:
a liquid glycol selected from the group consisting of a glycol containing n hydroxyl groups and from n to n+2 carbon atoms where n is 2 to 10, a glycol having the formula HO—$(C_2H_4O)_a$—H where a is 3 to 20 and a glycol having the formula HO—$(C_3H_6O)_b$—H where b is 2 to 15, said liquid glycol at a concentration of from about 50 weight percent to about 90 weight percent of said coating composition;
a coloring agent at a concentration in said composition of from about 0.05 weight percent to about 3 weight percent, such that, when said composition is applied as a thin coating to the occlusal surface of one tooth of a pair of occluding teeth and then the coated tooth and the uncoated tooth of said pair are brought into occluding relationship so that a portion of said coating is transferred to the occlusal surface of said uncoated tooth as a thin marking at each contact point between said teeth, said marking has sufficient color intensity to permit visual location of each contact point on the occlusal surface of said uncoated tooth; and
a thickening agent at a concentration in said composition of from about 10 weight percent to about 50 weight percent which comprises a material selected from the group consisting of:
A—a member selected from the group consisting of a solid glycol ester and a solid ethoxylated ester formed therefrom, said solid glycol ester having at least one free hydroxyl group and being an ester of a fatty acid containing from 12 to 22 carbon atoms and of a glycol selected from the group consisting of a glycol containing n hydroxyl groups and from n to n+2 carbon atoms where n is 2 to 10, a glycol having the formula HO—$(C_2H_4O)_d$—H where d is 3 to 27 and a glycol having the formula HO—$(C_3H_6O)_g$—H where g is 2 to 20, said ethoxylated ester being a reaction product of 2-30 moles of ethylene oxide and one mole of said solid glycol ester;
B—a mixture of (1) a component at a concentration of from about 3 weight percent to about 50 weight percent of said coating composition and selected from the group consisting of a glycol ester and an ethoxylated ester formed therefrom, said glycol ester having at least one free hydroxyl group and being an ester of a fatty acid containing from 12 to 22 carbon atoms and of a glycol selected from the group consisting of a glycol containing n hydroxyl groups and from n to n+2 carbon atoms where n is 2 to 10, a glycol having the formula HO—$(C_2H_4O)_x$—H where x is 3 to 27 and a glycol having the formula HO—$(C_3H_6O)_y$—H where y is 2 to 20, and of (2) a component selected from the group consisting of a fatty acid at a concentration of from about 1 weight percent to about 30 weight percent of said coating composition and containing from 12 to 22 carbon atoms, a fatty acid ester of a fatty acid containing 10 to 22 carbon atoms and of an aliphatic monohydroxyl alcohol containing from 1 to 4 carbon atoms, said fatty acid ester at a concentration of from about 1 weight percent to about 5 weight percent of said coating composition; a fatty alcohol at a concentration of from about 0.1 weight percent of about 5 weight percent of said coating composition and containing from 10 to 30 carbon atoms, an ethoxylated fatty alcohol at a concentration of from about 0.3 weight percent to about 2 weight percent of said coating composition and which is a reaction product of one mole of fatty alcohol containing from 10 to 30 carbon atoms and 2 to 30 moles of ethylene oxide, an aliphatic hydrocarbon oil at a concentration of from about 1 weight percent to about 10 weight percent of said coating composition, and an alkanolamine which is at a concentration of from about 1 percent to about 10 weight percent of said coating composition and which is a secondary or tertiary amine containing from 4 to b 9 carbon atoms, with each alkanol moiety thereof containing 2 to 3 carbon atoms; and C—a mixture of a solid fatty acid at a concentration of from about 7 weight percent to about 40 weight percent of said coating composition and containing 12 to 22 carbon atoms and an alkanolamine which is at a concentration which is about 0.1 to 1.0 of that needed to exactly neutralize said fatty acid in said mixture C and which is a secondary or tertiary amine containing from 4 to 9 carbon atoms, with each alkanol moiety thereof containing 2 to 3 carbon atoms;

said composition being in the form of a readily deformable paste which is capable of being smeared as a thin, immobile coating on the occlusal surface of said coated tooth, a portion of said coating capable of being transferred to the occlusal surface of said uncoated tooth when said pair of occluding teeth is brought into occluding relationship, as a thin marking at each contact point between said teeth, said coating being sufficiently thin to permit said occluding teeth to enter into a substantially unimpaired occluding relationship, the mixture of said liquid glycol and said thickening agent serving as a carrier for said coloring agent and being removable from said teeth by a water rinse.

2. The coating composition of claim 1 wherein said liquid glycol is at a concentration of from about 65 weight percent to about 85 weight percent of said composition.

3. The coating composition of claim 1 wherein said liquid glycol is selected from the group consisting of ethylene glycol, propylene glycol, glycerin, sorbitol, diethylene glycol, dipropylene glycol, diglycerin, polyethylene glycol and polypropylene glycol.

4. The coating composition of claim 3 wherein said liquid glycol is a mixture of glycerin and propylene glycol.

5. The coating composition of claim 1 wherein said coloring agent is a food coloring.

6. The coating composition of claim 1 wherein said coloring agent is at a concentration of from about 0.1 weight percent to about 2 weight percent of said composition.

7. The coating composition of claim 1 wherein said thickening agent is at a concentration of from about 15 weight percent to about 35 weight percent of said composition.

8. The coating composition of claim 1 wherein said member A is at a concentration of from about 15 weight percent to about 35 weight percent of said coating composition.

9. The coating composition of claim 1 wherein said member A is said solid glycol ester.

10. The coating composition of claim 1 wherein said member A is selected from the group consisting of the monostearate, monopalmitate and monolaurate of ethylene glycol, propylene glycol, glycerin, sorbitol, sucrose, diethylene glycol, dipropylene glycol, diglycerin, sorbitan, polyethylene glycol and polypropylene glycol, and the ethoxylated derivatives thereof.

11. The coating composition of claim 10 wherein said member A is glyceryl monostearate.

12. The coating composition of claim 1 wherein said component (1) in said mixture B is said glycol ester.

13. The coating composition of claim 1 wherein said component (1) in said mixture B is selected from the group consisting of the monooleate, monostearate, monopalmitate and monolaurate of ethylene glycol, propylene glycol, glycerin, sorbitol, sucrose, diethylene glycol, dipropylene glycol, diglycerin, sorbitan, polyethylene glycol and polypropylene glycol and the ethoxylated derivatives thereof.

14. The coating composition of claim 13 wherein said component (1) is glyceryl monostearate.

15. The coating composition of claim 1 wherein said component (1) is at a concentration of from about 5 weight percent to about 35 weight percent of said coating composition.

16. The coating composition of claim 1 wherein said fatty acid of said component (2) in said mixture B is selected from the group consisting of stearic, palmitic, lauric, myristic, oleic and linoleic acids.

17. The coating composition of claim 16 wherein said fatty acid is stearic acid.

18. The coating composition of claim 1 wherein said fatty acid of said component (2) in said mixture is at a concentration of from about 2 weight percent to about 15 weight percent of said coating composition.

19. The coating composition of claim 1 wherein said fatty acid ester of said component (2) in said mixture B is selected from the group consisting of methyl laurate, isopropyl myristate, isopropyl palmitate, n-butyl stearate, isopropyl isostearate and n-butyl oleate.

20. The coating composition of claim 19 wherein said fatty acid ester is isopropyl palmitate.

21. The coating composition of claim 1 wherein said fatty acid ester of said component (2) in said mixture B is at a concentration of from about 1 weight percent to about 3 weight percent of said coating composition.

22. The coating composition of claim 1 wherein said fatty alcohol of said component (2) in said mixture B is selected from the group consisting of palmityl, stearyl, myristyl, oleyl, cetyl and lauryl alcohols.

23. The coating composition of claim 22 wherein said fatty alcohol is cetyl alcohol.

24. The coating composition of claim 1 wherein said fatty alcohol is at a concentration of from about 2 weight percent to about 5 weight percent of said coating composition.

25. The coating composition of claim 1 wherein said ethoxylated fatty alcohol of said component (2) in said mixture B is selected from the group consisting of laureth-4, laureth-20, laureth-23, steareth-20, ceteth-10, ceteth-20, ceteth-28, polyoxyethylene (10) oleyl ether and polyoxyethylene (20) oleyl ether.

26. The coating composition of claim 25 wherein said ethoxylated fatty alcohol is laureth-23.

27. The coating composition of claim 1 wherein said ethoxylated fatty alcohol is at a concentration of from about 0.5 weight percent to about 1 weight percent of said coating composition.

28. The coating composition of claim 1 wherein said aliphatic hydrocarbon oil of said component (2) in said mixture B is mineral oil.

29. The coating composition of claim 1 wherein said hydrocarbon oil is at a concentration of from about 4 weight percent to about 7 weight percent of said coating composition.

30. The coating composition of claim 1 wherein said alkanolamine in said mixture C or of said component (2) in said mixture B is selected from the group consisting of diethanolamine, diisopropanolamine, triethanolamine, triisopropanolamine and N-methyldiethanolamine.

31. The coating composition of claim 30 wherein said alkanolamine is triisopropanolamine.

32. The coating composition of claim 1 wherein said alkanolamine is at a concentration of from about 1 weight percent to about 3 weight percent of said coating composition.

33. The coating composition of claim 1 wherein said fatty acid in said mixture C is selected from the group consisting of stearic, palmitic, lauric and myristic acids.

34. The coating composition of claim 33 wherein said fatty acid is stearic acid.

35. The coating composition of claim 1 wherein said fatty acid in said mixture C is at a concentration of from about 12 weight percent to about 30 weight percent of said coating composition.

* * * * *

UNITED STATES PATENT AND TRADEMARK OFFICE
CERTIFICATE OF CORRECTION

PATENT NO. : 4,198,243
DATED : April 15, 1980
INVENTOR(S) : Asami Tanaka

It is certified that error appears in the above-identified patent and that said Letters Patent are hereby corrected as shown below:

The title should read --COATING COMPOSITION--.

Columns 7 and 8, Table I, "oil orange No. $31^2$" should read --oil orange No. $31^{16}$--.

Columns 7 and 8, Table I, under heading "$\underline{5}$", "5" should read --2--.

Column 8, line 1, "EXAMPLE" should read --EXAMPLES--.

Column 12, line 63 "monohydroxyl" should read --monohydroxy--.

Column 12, line 68, "of" should read --to--.

Column 13, line 15, "b9" should read --9--.

Column 14, line 35, after "mixture" insert --B--.

Signed and Sealed this

Sixteenth Day of September 1980

[SEAL]

Attest:

SIDNEY A. DIAMOND

*Attesting Officer*  *Commissioner of Patents and Trademarks*